(12) United States Patent
Dufay

(10) Patent No.: US 11,426,326 B2
(45) Date of Patent: Aug. 30, 2022

(54) TREATMENT METHOD AND APPARATUS WITH A SYSTEM FOR CONTROLLING THE FLOW OF THE GASEOUS MEDIUM

(71) Applicant: VistaCare Medical, Lons le Saunier (FR)

(72) Inventor: François Dufay, Lons le Saunier (FR)

(73) Assignee: VistaCare Medical, Lons le Saunier (FR)

( * ) Notice: Subject to any disclaimer, the term of this patent is extended or adjusted under 35 U.S.C. 154(b) by 0 days.

(21) Appl. No.: 17/259,484

(22) PCT Filed: Jul. 11, 2019

(86) PCT No.: PCT/FR2019/051745
§ 371 (c)(1),
(2) Date: Jan. 11, 2021

(87) PCT Pub. No.: WO2020/012131
PCT Pub. Date: Jan. 16, 2020

(65) Prior Publication Data
US 2021/0290484 A1 Sep. 23, 2021

(30) Foreign Application Priority Data
Jul. 12, 2018 (FR) ...................... 1856414

(51) Int. Cl.
*A61H 33/06* (2006.01)
*A61H 33/14* (2006.01)
*A61H 33/00* (2006.01)

(52) U.S. Cl.
CPC ........... *A61H 33/066* (2013.01); *A61H 33/14* (2013.01); *A61H 33/601* (2013.01); *A61H 33/6005* (2013.01); *A61H 2033/143* (2013.01); *A61H 2201/105* (2013.01); *A61H 2201/165* (2013.01); *A61H 2203/0456* (2013.01)

(58) Field of Classification Search
CPC ..................................... A61H 33/066
USPC ..................................... 4/524, 535
See application file for complete search history.

(56) References Cited

U.S. PATENT DOCUMENTS

| 4,224,941 A | 9/1980 | Stivala |
| 2005/0191372 A1 | 9/2005 | Stenzler et al. |
| 2021/0106492 A1* | 4/2021 | Berdahl ............... A61F 9/0008 |

FOREIGN PATENT DOCUMENTS

| EP | 2260825 A1 | 12/2010 |
| FR | 3052662 A1 | 12/2017 |

OTHER PUBLICATIONS

International Search Report for PCT/FR2019/051745, dated Nov. 11, 2019, 10 pages.

* cited by examiner

*Primary Examiner* — Lori L Baker
(74) *Attorney, Agent, or Firm* — ArentFox Schiff LLP

(57) ABSTRACT

The invention relates to a treatment apparatus comprising an envelope that can be placed on or around a body part of a person such that the envelope has a positioning area (Z) for said body part of the person, the envelope being provided with an inlet (8) for a gaseous medium and an outlet for discharging the gaseous medium present in the envelope. According to the invention, the apparatus comprises a control system (11) for controlling the flow of the gaseous medium in order to direct the gaseous medium entering the envelope via the inlet (8) outside the positioning area (Z), and to homogenise the gaseous medium present in the envelope.

16 Claims, 5 Drawing Sheets

TREATMENT METHOD AND APPARATUS WITH A SYSTEM FOR CONTROLLING THE FLOW OF THE GASEOUS MEDIUM

CROSS-REFERENCE TO RELATED APPLICATIONS

This application is a National Stage of PCT/FR2019/051745, filed on Jul. 11, 2019, which claims priority to French Patent Application No. 1856414, filed on Jul. 12, 2018, the disclosures of which are hereby incorporated by reference in their entireties.

FIELD OF THE INVENTION

The present invention relates to the technical field of the topical or systemic, curative or preventive treatment of the body for therapeutic, esthetic and cosmetic applications in man and in beast, and more particularly the treatment of injured tissues, with or without breaking, with or without loss of substance.

BACKGROUND

In order to treat injured tissues or wounds, the prior art has proposed the application of dressings, and this presents the problems of contact between the dressing and the wound and the risk of microbial growth.

In order to avoid these problems, the prior art has proposed various treatment apparatuses aimed at exposing the injured tissues to a gaseous medium. For example, patent EP 2 309 954 describes a treatment apparatus comprising a cover able to be placed over or around an individual's body part that is to be treated. This cover is equipped with an inlet for a gaseous medium and with an outlet for removing the gaseous medium present inside the cover.

Patent application US 2005/191372 describes a device for treatment with gaseous nitric oxide comprising a chamber, a source of nitric oxide, a control valve and a pump. The chamber can be of any shape and made of any material, and comprises an inlet and an outlet for the gas. As a preference, this inlet and this outlet are positioned some distance apart so as to increase the time spent by the gas passing through the chamber. A control system provides control over the flow of gas at the valve and at the pump. According to the embodiment depicted in FIG. 2, a nozzle is fixed at the inlet in order to direct the nitric oxide onto the zone that is to be treated. According to the embodiment depicted in FIG. 4, the chamber further comprises an agitator to create turbulent conditions inside said chamber. The agitator thus refreshes the nitric oxide in the region of the zone that is to be treated.

Patent FR 3 052 662 describes a system for generating a gaseous mixture for a wound treatment closure comprising a gaseous-mixture generator, a treatment enclosure, a device for adding an additional gas and/or an aerosol, and a control unit. The treatment enclosure is designed to be placed over and/or around a part of the body of a patient so as to generate a treatment zone. The treatment enclosure comprises an inlet and an outlet for the gaseous mixture. The control unit provides control of the gaseous-mixture generator and defines a flowrate, a temperature and a composition for the gaseous mixture that is to be delivered.

Patent application EP 2 260 825 describes a device for generating a gaseous mixture, made up of gas and of liquid, for treating a patient. According to a first embodiment, that device comprises a means for covering the zone that is to be treated with an inlet and an outlet for the gaseous mixture, an adhesive part, sources of gas and of liquid, and a control means controlling in particular the pressure and the temperature. The gaseous-mixture inlet may comprise a valve to give a nonreturn effect.

U.S. Pat. No. 4,224,941 describes a device for administering a gaseous mixture to the skin of a patient, comprising an adhesive compress, a cylindrical component connected to the adhesive compress via one of its sides and connected by the other of its sides to a bag, an inlet and an outlet for the gaseous mixture being situated on said bag. The inlet is connected to a gaseous-mixture source via a connector.

SUMMARY OF THE INVENTION

It is apparent from the documents of the prior art that an apparatus that exposes injured tissues to a gaseous medium is associated with a device providing control of the atmosphere prevailing inside the cover. In particular, the temperature needs to be controlled because the temperature window for the treatment is generally narrow. Furthermore, the tissues must not be exposed to high temperatures for lengthy periods. In addition, in the therapeutic domain, it is important to control the oxygen concentration in order to limit, or even eliminate, the growth of aerobic or anaerobic bacteria.

The hygrometry of the injected gaseous medium is also controlled in order to optimize the regeneration of the injured tissues. In general, parameters such as the temperature, the hygrometry and the composition of the gaseous medium are controlled in such a way as to optimize the treatment to be performed on the injured tissues.

In practice, despite the control of the various parameters of the gaseous medium injected into the cover, it has been found that the changes to the injured tissues do not correspond to the change expected for the treatment applied. Aside from such a distortion in the expected results, the patient often feels pain or discomfort while the treatment is being carried out.

The applicant, to their credit, has discovered that the deficiencies obtained in the treatment originate not from the parameters adopted but rather are associated with the conditions under which the gaseous medium inside the treatment cover is applied. Specifically, it has been found that the atmosphere in contact with the injured tissues and prevailing inside the known treatment covers exhibits parameters the values of which do not correspond to the adopted or setpoint values.

The present invention seeks to overcome the disadvantages of the prior art by proposing a treatment apparatus aimed at exposing injured tissues to a gaseous medium inside a cover, and which is designed so that the conditions of application of the gaseous medium allow the treatment performed to be optimized.

In order to achieve such an objective, the treatment apparatus according to the invention comprises a cover able to be placed over or around part of the body of an individual such that the cover has a positioning zone for positioning said individual's body part, the cover being equipped with an inlet for a gaseous medium and with an outlet for removing the gaseous medium present in the cover. According to the invention, this apparatus comprises a system for controlling the flow of the gaseous medium in order to direct the gaseous medium entering the cover via the inlet away from the positioning zone and to homogenize the gaseous medium present inside the cover.

The treatment apparatus according to the invention prevents the gaseous medium from arriving directly onto the patient's skin and particularly onto the injured tissues, and this prevents the wound from drying out and allows it to heal, because the drying-out of the wound prevents such healing.

The apparatus according to the invention homogenizes the gaseous medium inside the cover before it comes into contact with the injured tissues. The flow of the gaseous medium inside the cover, according to a turbulent flow regimen, allows the atmosphere present inside the cover to be homogenized. This homogenization allows the parameters of the atmosphere in contact with the injured tissues to possess values corresponding to the adopted or setpoint values, this homogenization being obtained whatever the variations in these parameters.

Use of these conditions of application of the gaseous medium within the treatment cover means that the patient does not feel any pain or discomfort while the treatment is being performed.

According to one advantageous embodiment feature, the flow control system comprises a deflector modifying the direction of flow of the gaseous medium inside the cover, away from the positioning zone and creating a turbulent flow regimen.

According to a first embodiment, the deflector has an orientation surface for orienting the gaseous medium toward the internal surface of the cover and onto which the gaseous medium entering the cover via the inlet is directed.

According to a second embodiment, the deflector comprises a pipe with an elbow mounted on the inlet. Advantageously, the pipe with an elbow is mounted with the ability to rotate about its axis in order to regulate the orientation of the flow.

According to a preferred embodiment variant, the cover of the treatment apparatus according to the invention is equipped with a viewing device for viewing the positioning zone for said individual's body part, and the flow control system directs the gaseous medium toward the viewing device in order to defog same.

Specifically, the hygrometry level of the gaseous medium and the difference in temperature between the inside and the outside of the enclosure create conditions that encourage fogging, notably on the viewing device.

Channeling the gaseous medium toward the viewing system makes it possible to avoid or eliminate fogging so that therapeutic monitoring can be conducted effectively throughout the length of the treatment, whatever the temperatures inside and outside the cover.

It should be noted that the treatment apparatus according to the invention may comprise, by way of viewing device, a window created in the cover or an optical system with or without image capture.

In addition, the treatment apparatus according to the invention may further comprise a combination of at least one and/or the other of the following additional features:
- the inlet and the outlet are positioned side by side in divergent directions;
- the inlet and the outlet are created on a body that is removable with respect to the cover.

The treatment apparatus according to the invention aims to expose the injured tissues to a gaseous medium. In addition, the treatment apparatus according to the invention is designed to incorporate a liquid into the treatment cover to facilitate the washing of the wound and/or to eliminate substrates exuded by said wound. This method is known as instillation. In another application, the liquid injected into the treatment cover may be a medicinal product which is brought into direct contact with the wound in a therapeutic context.

For this purpose, the inlet of the treatment cover is designed to be connected to a source supplying liquid medium and the treatment cover is provided with a discharge outlet for removing the liquid medium, this outlet corresponding to the outlet for the gaseous medium or to an additional outlet created in the treatment cover.

The treatment apparatus according to the invention aims to expose the injured tissues to a gaseous medium but also to a liquid medium.

Another object of the invention is to propose a method for treating injured tissues using a treatment apparatus comprising a cover placed over or around a part of the body of an individual and equipped with an inlet for a gaseous medium and with an outlet for removing the gaseous medium present in the cover.

According to the invention, the method consists in controlling the flow of the gaseous medium in order to direct the gaseous medium away from the zone in which said individual's body part is positioned, and to homogenize the gaseous medium present inside the cover.

Advantageously, the method consists in creating turbulence in the flow of the gaseous medium inside the cover.

As a preference, the method consists in directing the gaseous medium toward a viewing device for viewing the individual's body part, so as to defog the viewing device.

According to a complementary method, a liquid medium is injected via the inlet of the cover and the liquid medium is removed from the cover via the gaseous-medium discharge outlet or via an additional outlet specific to the liquid medium.

According to one implementation, the method consists in orienting a pipe with an elbow mounted on the inlet of the cover so as to inject the liquid medium into the zone in which said individual's body part is positioned.

BRIEF DESCRIPTION OF THE SEVERAL VIEWS OF THE DRAWINGS

Various other features will become apparent from the description given hereinbelow with reference to the attached drawings which, by way of nonlimiting examples, depict embodiments of the subject matter of the invention.

DETAILED DESCRIPTION OF THE INVENTION

Figure 7:
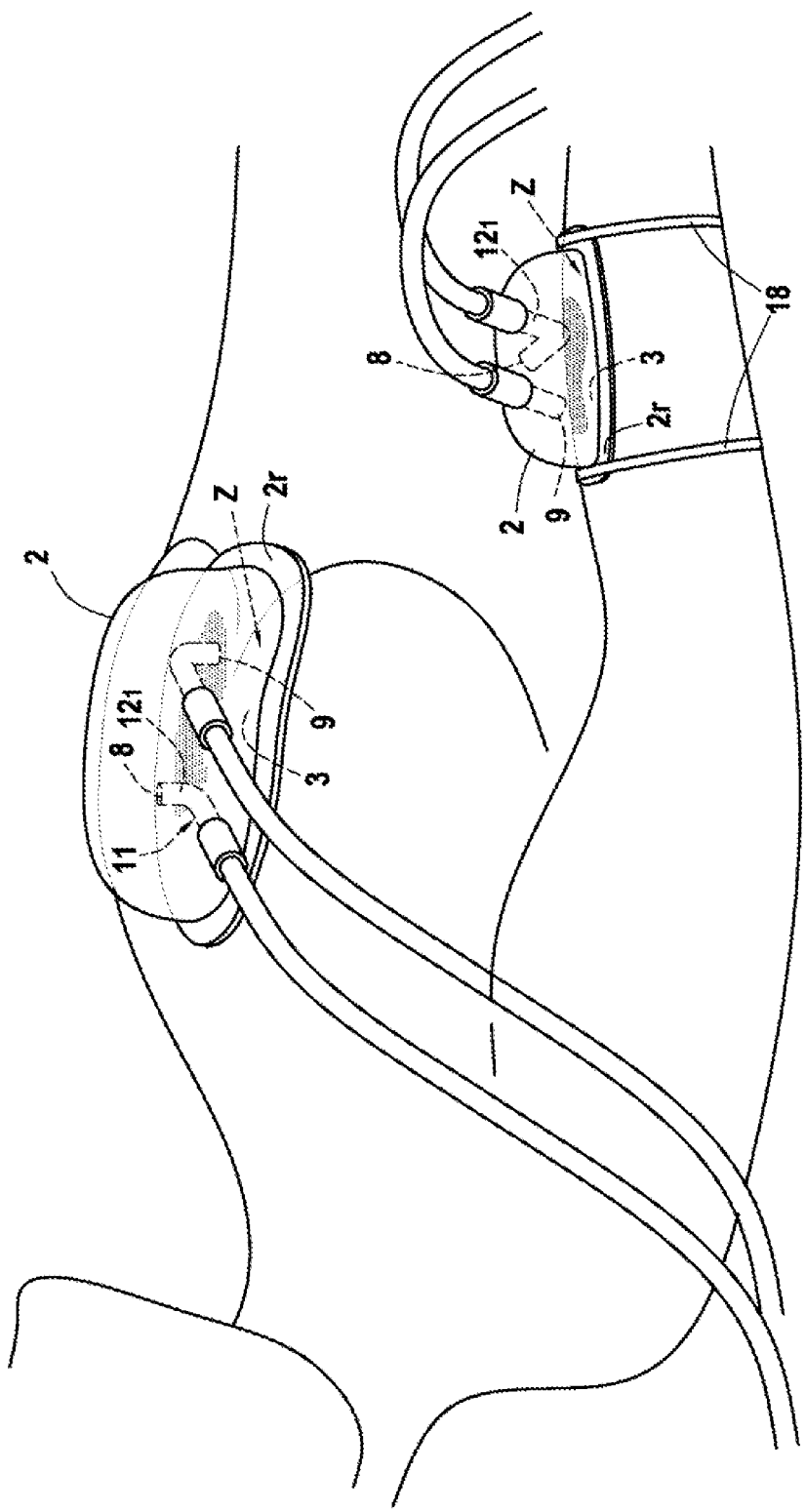
FIG. 7 shows other embodiments of a treatment apparatus according to the invention.
Figure 8:
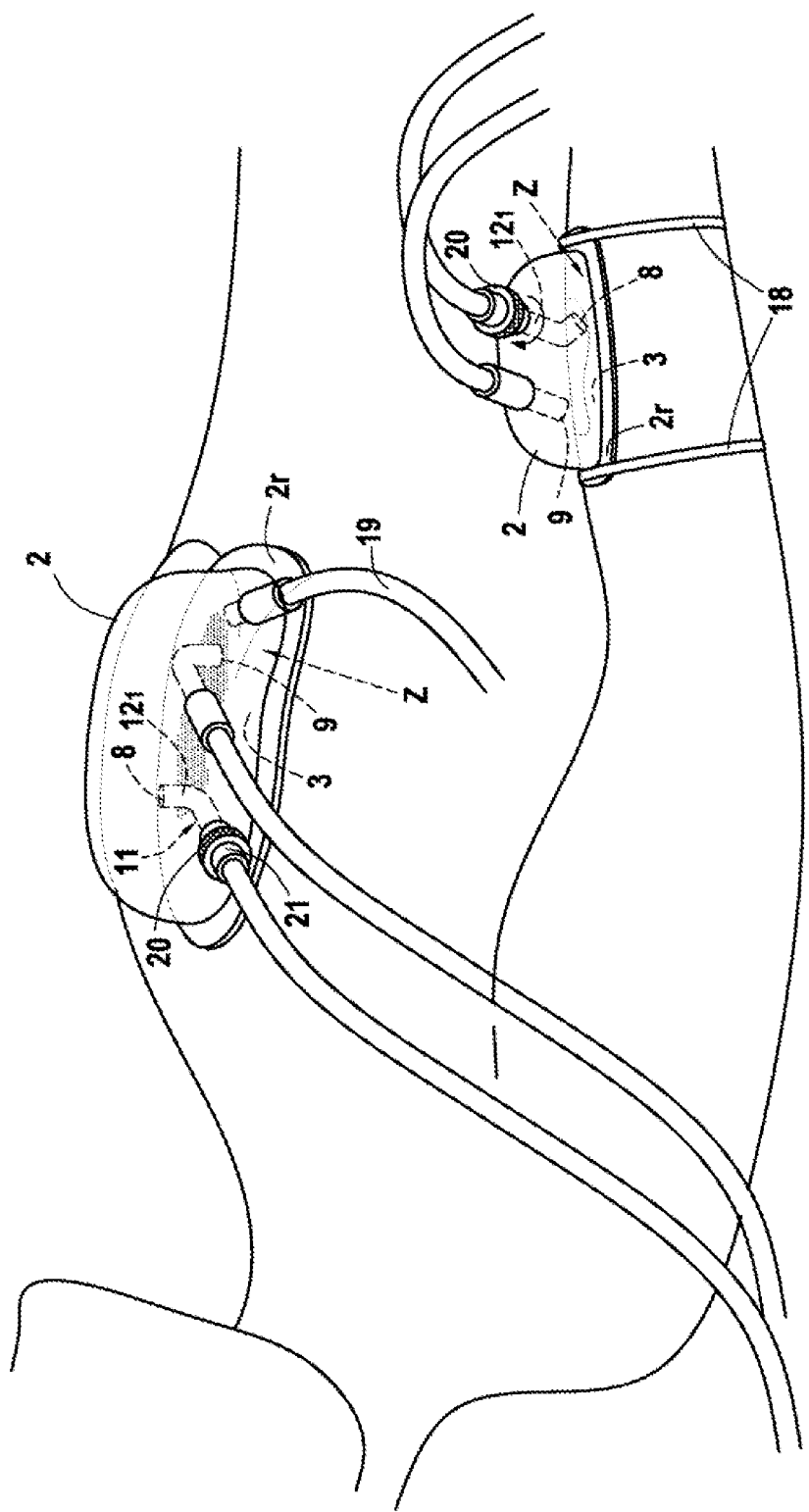
FIG. 8 illustrates another embodiment of a treatment apparatus according to the invention, employing a gaseous medium and a liquid medium.

The figures depict an apparatus 1 according to the invention comprising a treatment cover 2, able to be placed over or around an individual's body part 3 that has injured tissues to be treated with a gaseous medium in the general sense. In the example illustrated in FIGS. 1 to 6, the treatment cover 2 is intended to be placed around an individual's body part that is to be treated and, in particular, around an individual's leg 3. FIGS. 7 and 8 illustrate another embodiment for which the treatment cover 2 is able to be placed over an individual's body part 3, such as an individual's arm or thorax.

Of course, the treatment apparatus 1 according to the invention comprises a cover 2 of which the shape and dimensions are suited to the body part 3 that is to be treated. Whatever the body part 3 that is to be treated, the treatment cover 2 has a positioning zone Z to ensure that the injured tissues of said individual's body part can be in contact with the gaseous medium present inside this treatment cover 2. It should be understood that the positioning zone Z corresponds to the volume occupied by the injured tissues that are to be treated and possibly by a body part that does not need to be treated but is situated around or in the continuation of the injured tissues. The sizing of the treatment cover 2 takes account of this positioning zone Z so that when this zone Z is occupied by the body part 3 that is to be treated, the cover has, for the gaseous medium, a volume suited to performing the treatment on the injured tissues.

Figure 1:
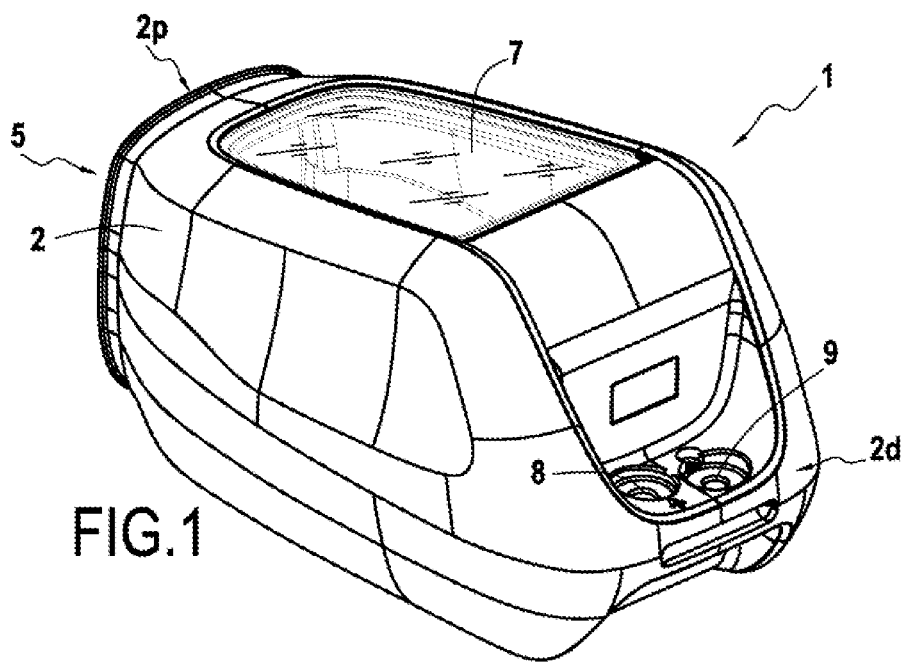
FIG. 1 is a perspective view of one embodiment of a treatment apparatus according to the invention.
Figure 2:
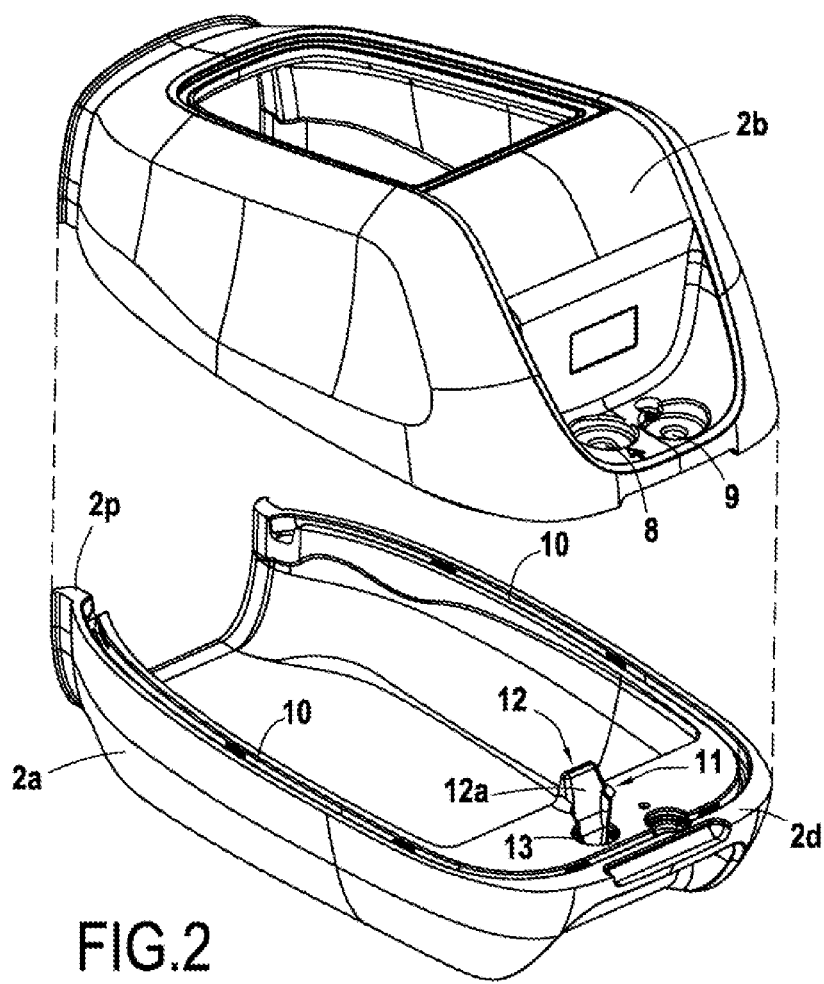
FIG. 2 is an exploded perspective view of the embodiment of the treatment apparatus illustrated in FIG. 1.
Figure 3:
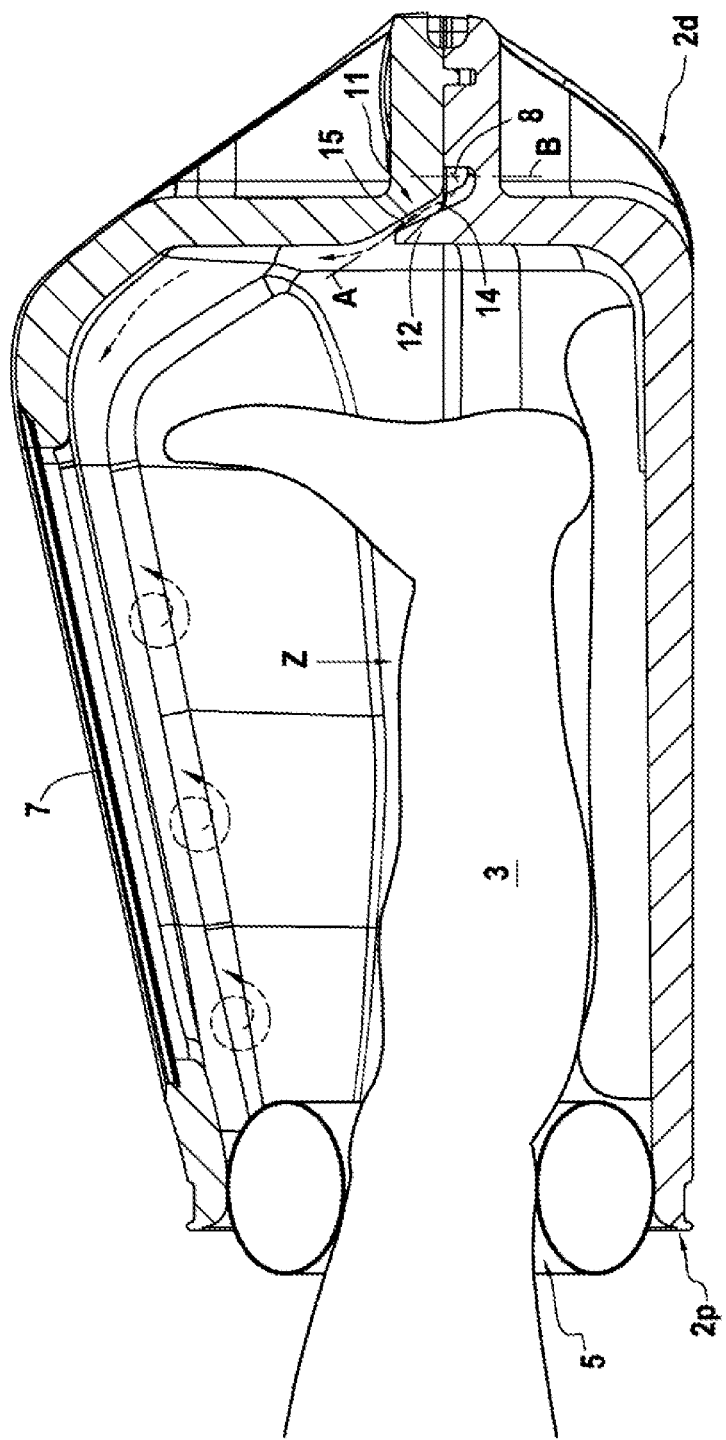
FIG. 3 is a side elevation in cross section of the treatment apparatus according to the invention, designed for treating part of an individual's leg.

In the example illustrated in FIGS. 1 to 6, the treatment cover 2 takes the form of an elongate casing, open at one end for the passage of the arm or of the leg, whereas in the example illustrated in FIGS. 7 and 8, the treatment cover 2 takes the form of a cloche that rests on an individual's body part. In the case of the example illustrated in FIGS. 1 to 6, the positioning zone Z for positioning the body part 3 that is to be treated is situated in the internal volume of the treatment cover 2 and some distance from this cover and corresponds to the volume occupied by the leg, as illustrated in FIG. 3. In the example illustrated in FIGS. 7 and 8, this positioning zone Z, which closes the treatment cover 2, extends opposite or facing the treatment cover and corresponds to a surface of the thorax or a surface of the arm.

In the example illustrated in FIGS. 1 to 6, the treatment cover 2 takes the form of a rigid casing made up for example of a bottom shell 2a and of a top shell 2b, which shells are intended to be assembled with one another to form, via their wall, a closed enclosure accessible via a passage 5 for the introduction of the body part 3 that is to be treated. The elongate cover 2 also has a proximal end 2p in which the passage 5 is created, and a distal end 2d situated opposite the proximal end 2p. In the example illustrated in FIGS. 7 and 8, the treatment cover 2 takes the form of a shell of hemispherical shape.

According to a preferred embodiment variant, the cover 2 is equipped with a device 7 for viewing the positioning zone Z for said individual's body part 3. According to the example illustrated in FIGS. 1 to 6, the cover 2 comprises, by way of viewing device 7, a window created in the top shell 2b and, more specifically, on the top face of the top shell 2b. The presence of the window 7 allows the condition of the injured tissues to be observed, and their progress monitored. In the example illustrated in FIGS. 7 and 8, the cover 2 is made from a transparent or translucent material in order to form the viewing device. Of course, it may be conceivable to create a window on the cloche-shaped enclosure illustrated in FIGS. 7 and 8.

The treatment cover 2 may be equipped with a viewing device 7 of a type different than a window as illustrated in the drawings. For example, the viewing device may be produced in the form of an optical system with or without image capture, such as a CCD sensor, an endoscope, a camera or an optical fiber.

In the conventional way, the treatment cover 2 is equipped with an inlet 8 for a gaseous medium and with an outlet 9 for removing the gaseous medium present inside the cover 2. The inlet 8 allows a gaseous medium of any suitable nature, such as, for example, oxygen-enriched or oxygen-impoverished air, to be introduced into the treatment cover 2. Typically, the inlet 8 is connected to an external circuit connected to a treatment machine which has not been depicted but is known per se and that allows a gaseous medium of which the various parameters such as, for example, the temperature, the hygrometry, the oxygen concentration or the pressure are controlled to be injected into the treatment cover.

In the example illustrated in FIGS. 1 to 6, the inlet 8 opens to the outside of the treatment cover, on the top shell 2b, at the distal end 2d, so as to be connected to the external circuit connected to the treatment machine.

The outlet 9 is connected, via an external circuit that has not been depicted, to a suction system that allows some of the atmosphere contained inside the treatment cover 2 to be removed in order to create circulation in the treatment cover 2. The outlet 9 is configured in such a way as to extract the homogenous atmosphere prevailing inside the cover rather than the gaseous medium that has just entered via the inlet 8. In the example illustrated in FIGS. 1 to 6, the outlet 9 is produced in the form of a duct 10 created in each of the lateral walls of the treatment cover, with its inlet situated at the proximal end 2p and opening, via an outlet that is common to the outside of the treatment cover 2, on the top shell 2b, at the distal end 2d. According to this embodiment variant, the inlet 8 and the outlet 9 open side by side, to the outside of the treatment cover, on the top shell 2b.

According to the invention, the apparatus 1 comprises a system 11 for controlling the flow of the gaseous medium inside the treatment cover 2 and designed to direct the gaseous medium entering the cover via the inlet 8 away from the positioning zone Z and to homogenize the gaseous medium present inside the cover 2. The treatment cover 2 is therefore equipped with the system 11 that provides control over the flow of the gaseous medium inside the treatment cover 2.

The flow control system 11 directs the gaseous medium away from the positioning zone Z thus preventing the gaseous medium from impinging directly at high speed on the patient's skin, notably on the injured tissues. Channeling the gaseous medium away from the positioning zone Z, namely away from said individual's body part that is to be treated, prevents the wound from drying out and allows it to heal. As will be explained in the following portion of the description, the flow control system 11 channels the gaseous medium particularly toward the treatment cover 2. The gaseous medium entering via the inlet 8 is thus directed directly toward the cover.

The flow control system 11 also homogenizes the gaseous medium inside the cover before it comes into contact with the injured tissues. The flow control system 11 creates turbulence in the flow of the gaseous medium in the treatment cover 2 so as to homogenize the atmosphere present inside the cover. Having the gaseous medium flow in a turbulent regimen and away from the positioning zone Z makes it possible to obtain an atmosphere that is homogenous before it comes into contact with the injured tissues. The result of this is that the atmosphere in contact with the injured tissues conforms to the desired parameters.

The system 11 for controlling the flow of the gaseous medium may be produced in any suitable way for directing the gaseous medium away from the positioning zone Z and for homogenizing the gaseous medium present inside the cover 2. In general, the flow control system 11 comprises a deflector that alters the direction of flow of the gaseous medium inside the cover 2, away from the positioning zone Z and creating a turbulent flow regimen.

In the embodiment illustrated in FIGS. 1 to 6, the control system 11 comprises a deflector 12 onto which the gaseous medium entering the treatment cover via the inlet 8 is directed. The gaseous medium enters the treatment cover 2 at a velocity suited to ensuring a turbulent flow regimen. Typically, the gaseous medium has, at the inlet 8, a velocity high enough to allow the incoming stream to spread throughout the volume of the treatment enclosure.

Figure 4:
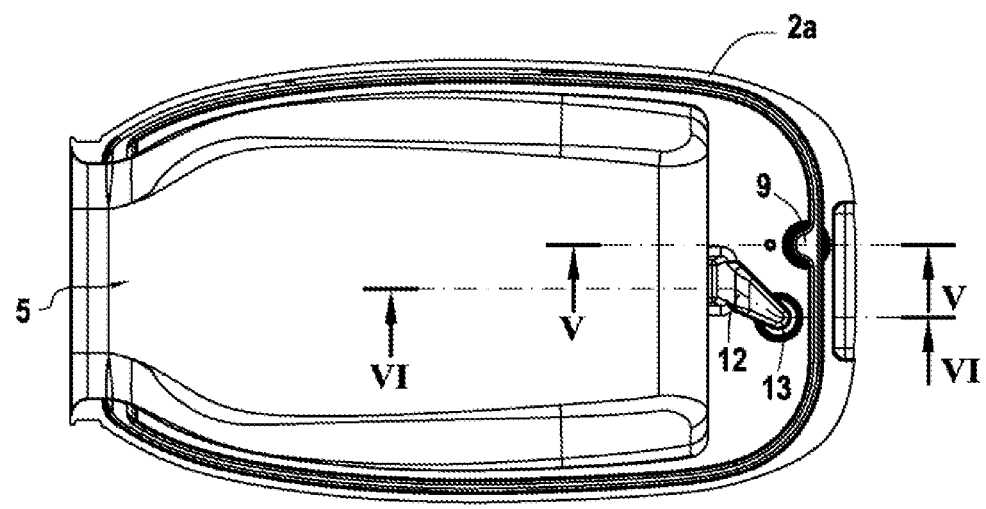
FIG. 4 is a view from above of the lower part of the treatment apparatus according to the invention.
Figure 5:
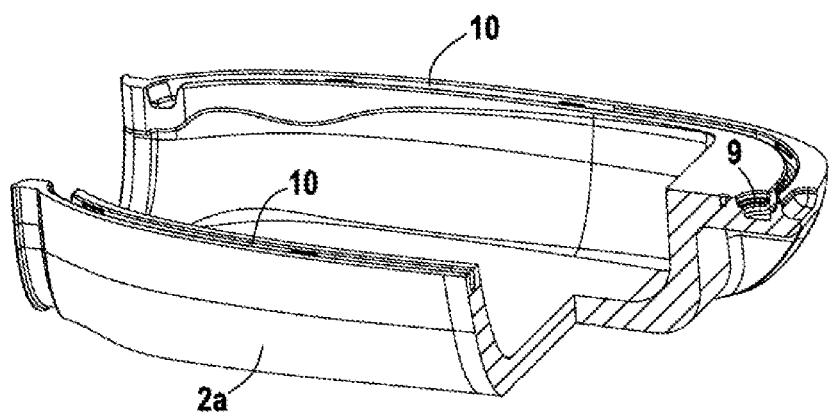
FIGS. 5 and 6 are perspective views partially sectioned on lines V-V and VI-VI, respectively, showing the lower part of the treatment apparatus according to the invention.
Figure 6:
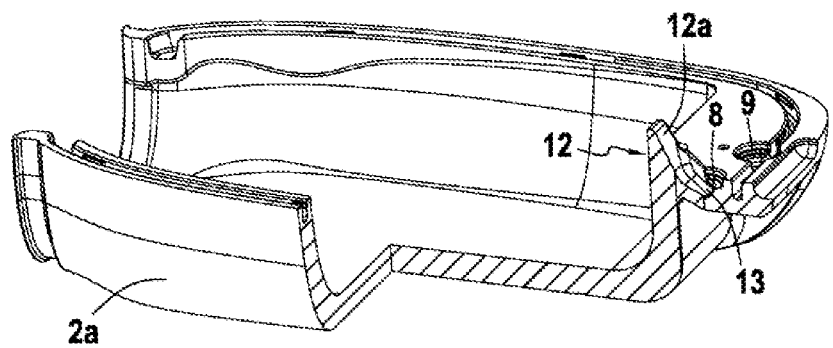

As is more specifically apparent in FIGS. 2, 4 and 6, the inlet 8 comprises a well 13 created in the top shell 2b and opening to the outside of the treatment cover. This well 13 is also created in the bottom shell 2a, being extended by a deflection duct 14 opening to the inside of the treatment cover 2. This deflection duct 14 is delimited between the deflector 12 and the internal surface 15 of the top shell 2b. The deflector 12 is created inside the treatment cover 2, at the distal end 2d thereof.

According to one advantageous embodiment feature, the deflector 12 has an orientation surface 12a for orienting the gaseous medium toward the internal surface of the treatment cover. In the example illustrated, the deflector 12 directs the gaseous medium in such a way that its flow follows the internal surface of the top shell 2b, from its lower part to its upper part and from its distal part 2d toward its proximal part 2p.

Advantageously, the deflector 12 has an orientation surface 12a situated facing the wall 15 of the treatment cover and delimiting the deflection duct 14. This orientation surface 12a has an axis of extension A which, with the axis B of the inlet 8, makes an angle comprised between 10 and 170°.

According to another advantageous embodiment feature, this orientation surface 12a of the deflector is planar or curved and may or may not have turned-up edges.

In instances in which the treatment cover 2 is equipped with a viewing device 7, the flow control system 11 directs the gaseous medium toward the viewing device in order to defog it. As is apparent from FIGS. 1 to 6, the flow of gaseous medium from the inlet 8 is directed in such a way as to brush across the window 7 and defog same.

It is apparent from the foregoing description that the gaseous medium that enters the distal end 2d of the treatment cover 2 is channeled toward the wall of the top shell 2b, from its lower part to its upper part, being directed toward the proximal part 2p of the treatment cover, exhibiting a turbulent flow as indicated in FIG. 3. The extraction of the gaseous medium present in the treatment cover 2 is performed at the proximal part 2p, via the ducts 10 connected to the outlet 9.

In the embodiment illustrated in FIGS. 7 and 8, the flow control system 11 comprises, by way of deflector, a pipe or duct with an elbow $12_1$ for admitting the gaseous medium and mounted on the inlet 8 in order to direct the gaseous medium away from the positioning zone Z and to homogenize the gaseous medium present in the cover 2. According to this embodiment, the treatment cover 2 takes the form of a hollow casing of elongate or hemispherical shape, provided with a rim 2r that comes to bear against the individual's body. This rim 2r can be used to secure the apparatus to the body using, for example, a strap or a cuff 18.

The treatment cover 2 is provided with an inlet 8 equipped with a pipe or a duct with an elbow $12_1$, mounted to direct the gaseous medium away from the positioning zone Z and to homogenize the gaseous medium present inside the cover 2. As the positioning zone Z extends in the plane passing through the rim via which the treatment cover is supported, the inlet 8 is created in the vicinity of this rim with the pipe directed toward the wall of the cover, namely in the opposite direction to the plane passing through the support rim 2r. The pipe or duct with an elbow $12_1$ delivers the gaseous medium at a velocity suitable for obtaining turbulent flow inside the treatment cover 2.

The pipe or duct with an elbow $12_1$ is designed to direct the gaseous medium toward the viewing device consisting, in the example illustrated in FIGS. 7 and 8, of all or part of the treatment cover 2 designed to form a window.

According to one advantageous embodiment feature, the inlet 8 and the outlet 9 are positioned side by side but in divergent directions so as to allow the gaseous medium inside the treatment cover 2 to circulate. With such an arrangement, the inlet 8 and the outlet 9 are arranged on a body, not depicted, mounted removably with respect to the treatment cover 2. Thus, this inlet 8 and the outlet 9 can be fitted to different treatment covers 2 having shapes suited to the body parts that are to be treated.

In instances in which the treatment apparatus comprises a device for viewing the individual's body part, the method consists in directing the gaseous medium toward a device for viewing the individual's body part in order to defog the viewing device.

It is apparent from the foregoing description that the treatment apparatus 1 according to the invention allows injured tissues to be exposed, inside a cover, to a gaseous medium while ensuring that the conditions of application of the gaseous medium optimize the treatment performed. According to one advantageous embodiment, the treatment apparatus 1 according to the invention also allows a liquid medium of any type, such as a physiological liquid in the context of the cleaning of a wound or an active medicinal liquid in the case of a specific treatment, also to be incorporated into the treatment cover 2.

According to this embodiment which is illustrated in FIG. 8, the inlet 8 of the treatment apparatus 1 is designed to be connected to a liquid-medium supply source. The injection of the liquid medium can be achieved using the external circuit used for injecting the gaseous medium and also connected to this liquid-medium supply source. The liquid medium may be injected using a specific circuit communicating with a liquid-medium supply source and connected, upstream of the inlet 8, to the external circuit used for injecting the gaseous medium.

The cover 2 is provided with a discharge outlet for the liquid medium and which corresponds either to the gaseous-medium outlet 9 as illustrated in the drawings by the cover worn on the arm of an individual or else to an additional outlet 19 specifically for the extraction of the liquid medium. This additional outlet 19 is of course placed at the lowest point of the cover as illustrated in the drawings by the cover worn on the thorax of an individual. Of course, the cover 2 is mounted in a fluidtight manner on an individual's body part using the strap or the cuff 18 and/or a sealing strip added at the rim 2r.

According to one advantageous feature of this embodiment, the pipe or duct with an elbow $12_1$ that forms the deflector is mounted with the ability to rotate about its axis in order to adjust the orientation of the flow inside the cover 2. This pipe or duct with an elbow $12_1$ can be manipulated from outside the cover using any suitable means such as a knurled ring 20 mounted securely on an extension of the pipe with an elbow $12_1$ projecting out from the cover. This knurled ring 20 is guided in rotation on a coupling 21 mounted fixedly and fluidtightly on the cover.

Using the knurled ring 20, the inlet 8 can be oriented either upward (toward the window) or downward (toward the wound) according to the fluidic substrate (liquid or gas) employed by the user. It should be noted that the continuation of the pipe or duct with an elbow $12_1$ may have a telescopic nature so that it can be extended lengthwise to make the orientation of the inlet 8 easier.

When a liquid (medicinal and/or washing, etc. liquid) is administered, the treatment apparatus according to the invention allows the stream of liquid to be directed onto the wound in order to facilitate the cleaning of the wound or to apply therapeutic or antibacterial elements thereto. The gaseous-medium inlet 8 may thus be used for injecting liquids of all types: physiological liquid in the context of the cleaning of a wound, medicinally active liquid in the case of a specific treatment.

The apparatus according to the invention offers the ability to perform a method of treating injured tissues that consists in controlling the flow of the gaseous medium in order to direct the gaseous medium away from the zone Z in which said individual's body part is positioned, but also in injecting a liquid medium via the inlet 8 of the cover and in removing a liquid medium from the cover via the gaseous-medium discharge outlet 9 or via an additional outlet 19. The method advantageously consists in orienting the pipe or duct with an elbow $12_1$, which is mounted on the inlet 8, for injecting the liquid medium into the zone Z in which the individual's body part exhibiting the injured tissues is positioned.

The invention is not restricted to the examples described and depicted because various modifications can be made thereto without departing from its scope.

The invention claimed is:

1. A treatment apparatus comprising:
 a cover sized and configured for placement over or around a user's body part, said cover includes a positioning zone for positioning the user's body part therein, and said cover further includes an inlet for a gaseous medium and with an outlet for removing said gaseous medium from said cover, and a flow control system for controlling the flow of said gaseous medium in order to direct the gaseous medium, wherein the flow control system comprises a deflector for modifying the direction of flow of the gaseous medium inside the cover, away from the positioning zone and creating a turbulent flow regimen to homogenize the gaseous medium present inside the cover.

2. The treatment apparatus of claim 1, wherein the deflector includes an orientation surface for orienting the gaseous medium toward an internal surface of the cover and onto which the gaseous medium entering the cover via the inlet is directed.

3. The treatment apparatus of claim 1, wherein the deflector comprises a pipe with an elbow mounted on the inlet.

4. The treatment apparatus of claim 3, wherein the deflector comprises a pipe with an elbow mounted rotatable about an axis for regulating an orientation of said flow.

5. The treatment apparatus of claim 1, wherein the cover includes a viewing device for viewing the positioning zone for a user's body part.

6. The treatment apparatus of claim 1, wherein the inlet and the outlet are positioned side by side in divergent directions.

7. The treatment apparatus of claim 1, wherein the inlet and the outlet are on a removable body that is removable from the cover.

8. The treatment apparatus of claim 5, further comprising a window created in the cover or an optical system with or without image capture.

9. The treatment apparatus of claim 1, wherein the inlet is designed to be connected to a source supplying liquid medium and in that the cover is provided with a discharge outlet for removing the liquid medium, this outlet corresponding to the outlet for the gaseous medium or to an additional outlet created in the cover.

10. A method for treating injured tissues using a treatment apparatus of claim 1, comprising:
 placing the cover over or around a user's body part; and
 controlling flow of a gaseous medium in order to direct the gaseous medium away from the zone in which the user's body part is positioned, and to homogenize the gaseous medium present inside the cover.

11. The method of claim 10, further comprising creating turbulence in the flow of the gaseous medium inside the cover.

12. The method of claim 10, further comprising directing the gaseous medium toward a viewing device for viewing the individual's body part, so as to defog the viewing device.

13. The method of claim 10, further comprising injecting a liquid medium via the inlet of the cover and in removing a liquid medium from the cover via the gaseous medium discharge outlet or via an additional outlet specific to the liquid medium.

14. The method of claim 13, further comprising orienting a pipe with an elbow mounted on the inlet so as to inject the liquid medium into the zone in which said individual's body part is positioned.

15. The treatment apparatus of claim 5, wherein the flow control system is capable of directing the gaseous medium toward the viewing device to defog the viewing device.

16. The method of claim 13, further comprising modifying the direction of flow of the gaseous medium inside the cover, away from the positioning zone and creating a turbulent flow regimen.

* * * * *